US008246688B2

(12) United States Patent
Hagen

(10) Patent No.: US 8,246,688 B2
(45) Date of Patent: Aug. 21, 2012

(54) KNEE ENDOPROSTHESIS

(75) Inventor: Thomas Hagen, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 46 days.

(21) Appl. No.: 12/807,573

(22) Filed: Sep. 7, 2010

(65) Prior Publication Data

US 2011/0071644 A1 Mar. 24, 2011

Related U.S. Application Data

(63) Continuation of application No. PCT/EP2009/000976, filed on Feb. 12, 2009.

(30) Foreign Application Priority Data

Apr. 5, 2008 (DE) .......................... 10 2008 017 394

(51) Int. Cl.
A61F 2/38 (2006.01)
(52) U.S. Cl. ................. 623/20.28; 623/14.12; 623/20.22
(58) Field of Classification Search ............... 623/14.12, 623/20.14, 20.15, 20.22, 20.28–20.33
See application file for complete search history.

(56) References Cited

U.S. PATENT DOCUMENTS

| 5,064,437 | A | 11/1991 | Stock et al. | |
|---|---|---|---|---|
| 5,871,542 | A | 2/1999 | Goodfellow et al. | |
| 6,013,103 | A | 1/2000 | Kaufman et al. | |
| 6,190,415 | B1 * | 2/2001 | Cooke et al. ............... | 623/20.33 |
| 2006/0195195 | A1 | 8/2006 | Burstein et al. | |
| 2008/0033567 | A1 | 2/2008 | Stchur | |

FOREIGN PATENT DOCUMENTS

| DE | 39 08 958 | 9/1990 |
|---|---|---|
| DE | 40 09 360 | 8/1991 |
| DE | 100 12 060 | 9/2001 |
| DE | 695 22 481 | 12/2001 |
| EP | 0 734 701 | 10/1996 |
| EP | 1 584 309 | 10/2005 |
| WO | 03/028586 | 4/2003 |

* cited by examiner

Primary Examiner — David H Willse
Assistant Examiner — Javier Blanco
(74) Attorney, Agent, or Firm — Lipsitz & McAllister, LLC

(57) ABSTRACT

In a knee endoprosthesis comprising a tibia part, a femur part having two condylar surfaces, and a meniscus part arranged between the femur part and the tibia part, the meniscus part having on its upper side two bearing shells for receiving and mounting the condylar surfaces of the femur part and having on its underside a meniscus-bearing surface which rests in a displaceable manner on a tibia-bearing surface on the upper side of the tibia part, in order to allow as large a bending angle as possible, with best possible adaptation to the anatomy of the natural knee joint, it is proposed that the meniscus-bearing surface and the tibia-bearing surface each have a spherical projection or a spherical recess offset in a medial or a lateral direction in relation to their center, that the spherical projection on one of the two bearing surfaces engage the spherical recess of the other bearing surface and thereby form a ball bearing-like mounting of the meniscus part on the tibia part, and that in the lateral or medial part of the two bearing surfaces, these bearing surfaces form supporting areas bearing on each other, which are curved in a dorsal-ventral direction and have a radius of curvature there, which is greater than the radius of curvature of the spherical projection and the spherical recess by at least the factor 2.5.

4 Claims, 8 Drawing Sheets

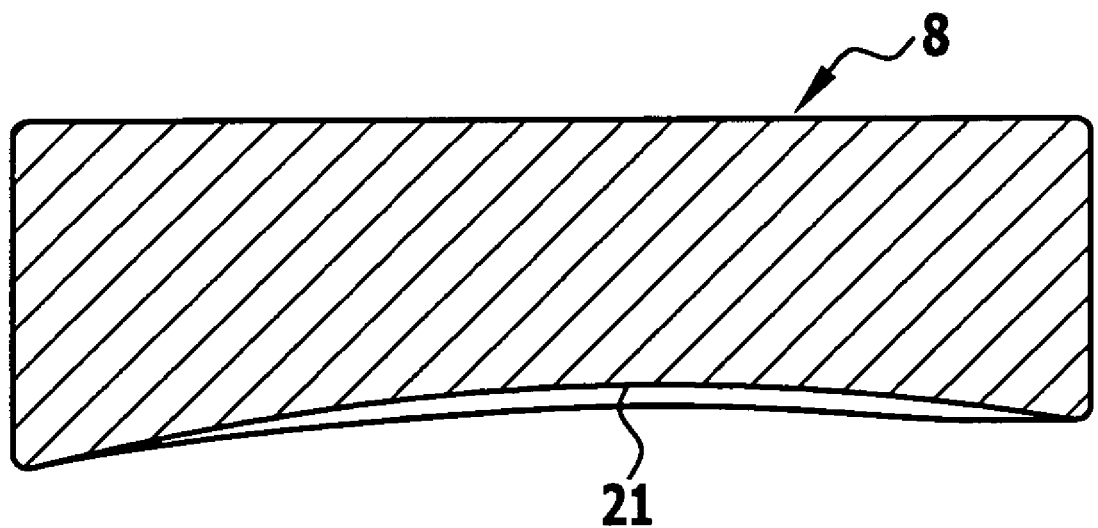

KNEE ENDOPROSTHESIS

This application is a continuation of international application No. PCT/EP2009/000976 filed on Feb. 12, 2009 and claims the benefit of German Patent Application No. 10 2008 017 394.0 filed on Apr. 5, 2008.

The present disclosure relates to the subject matter disclosed in international application No. PCT/EP2009/000976 of Feb. 12, 2009 and German application No. 10 2008 017 394.0 of Apr. 5, 2008, which are incorporated herein by reference in their entirety and for all purposes.

BACKGROUND OF THE INVENTION

The invention relates to a knee endoprosthesis comprising a tibia part, a femur part having two condylar surfaces, and a meniscus part arranged between the femur part and the tibia part, the meniscus part having on its upper side two bearing shells for receiving and mounting the condylar surfaces of the femur part and having on its underside a meniscus-bearing surface which rests in a displaceable manner on a tibia-bearing surface on the upper side of the tibia part.

A knee endoprosthesis of this kind is described in, for example, U.S. Pat. No. 6,013,103. In this previously known knee endoprosthesis, the tibia-bearing surface is of flat configuration and rests on the flat upper side of the tibia part. The displacement of the meniscus part relative to the tibia part takes place as pure parallel displacement of the meniscus part parallel to the plane of the tibia-bearing surface and the upper side of the tibia part. In unicondylar knee endoprostheses, too, it is known to mount a meniscus part, which in this case has only one bearing shell for the mounting of a femoral condyle, with a flat meniscus-bearing surface on a likewise flat tibia-bearing surface (EP 1 584 309 A1).

In knee endoprostheses of this kind, the meniscus part can be displaced and also rotated towards various directions relative to the tibia part, with the rotation taking place, as a rule, about the center of the meniscus part. In some cases, peg-shaped guides are provided for this purpose (U.S. Pat. No. 6,013,103). It is, however, also known to mount the meniscus part on the tibia part such that a rotation takes place about an axis of rotation which is offset in a medial direction in relation to the center of the meniscus part (U.S. Pat. No. 6,013,103). To achieve this, special guides, for example, lateral walls, must be provided on the tibia part for the meniscus part.

In practice, it has been found that with knee endoprostheses of such construction the anatomical relations can be reproduced relatively well, but difficulties may arise due to this special construction limiting the attainable bending angle between femur and tibia, as the meniscus part, which moves in only one plane relative to the tibia part, restricts the movement of the bones. In the case of high bending angles, the bones may strike the meniscus part, thereby restricting the bending angle.

The object underlying the invention is to so construct a generic knee endoprosthesis that in addition to optimum reproduction of the anatomical characteristics of the healthy knee joint, it allows, in particular, a high bending angle.

SUMMARY OF THE INVENTION

The object is accomplished, in accordance with the invention, in a knee endoprosthesis of the kind described at the outset in that the meniscus-bearing surface and the tibia-bearing surface each have a spherical projection or a spherical recess offset in a medial or a lateral direction in relation to their center, in that the spherical projection on one of the two bearing surfaces engages the spherical recess of the other bearing surface and thereby forms a ball bearing-like mounting of the meniscus part on the tibia part, and in that in the lateral or medial part of the two bearing surfaces, these bearing surfaces form supporting areas bearing on each other, which are curved in a dorsal-ventral direction and have a radius of curvature there, which is greater than the radius of curvature of the spherical projection and the spherical recess by at least the factor 2.5.

In such a configuration, the projection and the recess of the meniscus part and the tibia part engaging each other in the manner of a ball bearing form a ball bearing-like mounting which, upon rotation of the meniscus part on the tibia part, defines an axis of rotation which is offset in a medial or a lateral direction in relation to the center of the meniscus part. This ball bearing-like mounting also allows in addition to the rotation of the meniscus part relative to the tibia part a pivotal movement of the meniscus part on the tibia part, with the pivot axis extending in a medial-lateral direction and therefore substantially perpendicularly to the axis of rotation formed by the ball bearing-like mounting, which, in turn, is arranged substantially parallel to the tibial longitudinal axis. The meniscus part can be lowered in both a ventral and a dorsal direction at its outer edges by this pivotal movement, and the risk is thereby reduced that the meniscus part will impede the bending of the femur relative to the tibia also at large bending angles, i.e., larger bending angles are made possible. A further achievement is that the meniscus part, upon rotation about an axis extending substantially parallel to the tibial longitudinal axis, is rotated about a point of rotation which is offset in a medial or a lateral direction in relation to the center of the meniscus part and therefore corresponds substantially to the anatomical structures of the healthy knee joint or the requirements of the individual ligaments.

The constructional features described therefore make it possible for the meniscus part to move multidimensionally. This possibility goes beyond the pure parallel displacement in one plane and, in addition, ensures in a relatively simple way a defined rotation about a point of rotation lying outside the center. The ball bearing-like mounting of meniscus part and tibia part enables not only the rotation about this axis of rotation extending parallel to the tibial longitudinal axis, but also the pivotal movement about the pivot axis extending transversely thereto in a medial-lateral direction, with the ball bearing-like mounting being maintained in each case.

Furthermore, the rotational and pivotal movement of the meniscus part relative to the tibia part takes place as a result of the condylar surfaces of the femur being rolled off and displaced in the bearing shells on the upper side of the meniscus part when the femur is pivoted. The condylar surfaces exert lateral forces on the meniscus part, which displace and also positively rotate and pivot the meniscus part relative to the tibia part. In particular, when the femur is bent relative to the tibia, a rotation of the tibia about the longitudinal axis is also obtained in this way as a result of the meniscus part being rotated about the ball bearing-like mounting. This also corresponds to the anatomical features of the natural knee joint.

The larger radius of curvature of the supporting areas in relation to the radius of curvature of the spherical projection and the spherical recess ensures that the meniscus part and the tibia part maintain their ball bearing-like mounting in the area of the projection and the recess when the meniscus part is displaced relative to the tibia part, so that this displacement is transformed into a rotating and pivoting of the meniscus part relative to the tibia part, with the mounting being maintained in the area of the projection and the recess.

It may be provided that the supporting areas are only curved in a dorsal-ventral direction, but not transversely thereto. As a result of this, however, it cannot be ensured that the supporting areas are in contact over the whole surface throughout the entire range of rotation when the meniscus part is rotated relative to the tibia part. Such contact over the whole surface can only be achieved in certain angular ranges.

A better conformance of the contact surfaces of the supporting areas is achieved when, in accordance with a preferred embodiment, it is provided that the supporting areas of the two bearing surfaces are also curved in a lateral-medial direction. Also, such a configuration has a stabilizing effect as the additional curvature of the supporting areas in a lateral-medial direction counteracts the lateral displacement of the meniscus part relative to the tibia part in a lateral-medial direction.

In a first preferred embodiment, it is provided that the supporting areas in the lateral part of the two bearing surfaces are parts of a spherical surface whose radius is greater than the radius of the spherical projection and the spherical recess by at least the factor 2.5, the center points of the spherical projection and the spherical recess being offset in a medial or a lateral direction and the center point of the spherical surface then in a lateral or a medial direction in relation to the center of the bearing surfaces. With the construction of the supporting areas as spherical surface, a substantial surface-to-surface contact of the supporting areas can be approximately achieved over a larger angular range, but, even in this case, it is not possible to ensure such a surface-to-surface contact in large areas throughout the entire range of rotation of the meniscus part.

In accordance with a further preferred embodiment, it is therefore expedient for the supporting areas to extend along one or more lines, which result as line of intersection of two cylinder surfaces, namely a perpendicular cylinder surface whose center axis passes through the center point of the spherical projection and the spherical recess and extends substantially parallel to the tibial longitudinal axis, and a horizontal cylinder surface whose center axis passes through the center point defined by the curvature extending in a dorsal-ventral direction and extends substantially in a medial-lateral direction. When the supporting areas are configured in this way, a contacting of the supporting areas over the whole surface also results over a larger angular range when the implant part is rotated relative to the tibia part about an axis of rotation which coincides with the center axis of the perpendicular cylinder surface. Also the surface pressure and hence the wear can thereby be reduced.

In a particularly preferred embodiment it is provided that the projection and the recess and the supporting areas extend substantially as far as a common horizontal plane of the meniscus part, i.e., end approximately at the same level of the meniscus part.

The ball bearing-like mounting of the meniscus part on the tibia, which is achieved by a recess and a projection engaging the recess, may comprise both a projection on the meniscus part and a corresponding recess on the tibia part and a projection on the tibia part and a corresponding recess on the meniscus part i.e., a reversal is possible here. The same applies to the curvature of the supporting areas in a lateral-medial direction. This curvature may be so configured that the supporting area on the tibia part is curved upwardly or downwardly, whereas, of course, the curvature in a lateral-medial direction on the meniscus part then extends in the opposite direction.

The curvature of the supporting areas in a ventral-dorsal direction, however, must always be chosen so that the meniscus part, upon pivotal movement in a ventral direction, lowers the ventral outer edge and, upon pivotal movement in a dorsal direction, the dorsal outer edge, i.e., this curvature must always extend such that the center point of the curvature is arranged below the bearing surface between meniscus part and tibia part.

The following description of preferred embodiments of the invention serves in conjunction with the drawings for further explanation.

BRIEF DESCRIPTION OF THE DRAWINGS

FIG. 8 shows a sectional view taken along line 8-8 in FIG. 3.

DETAILED DESCRIPTION OF THE INVENTION

Figure 1:
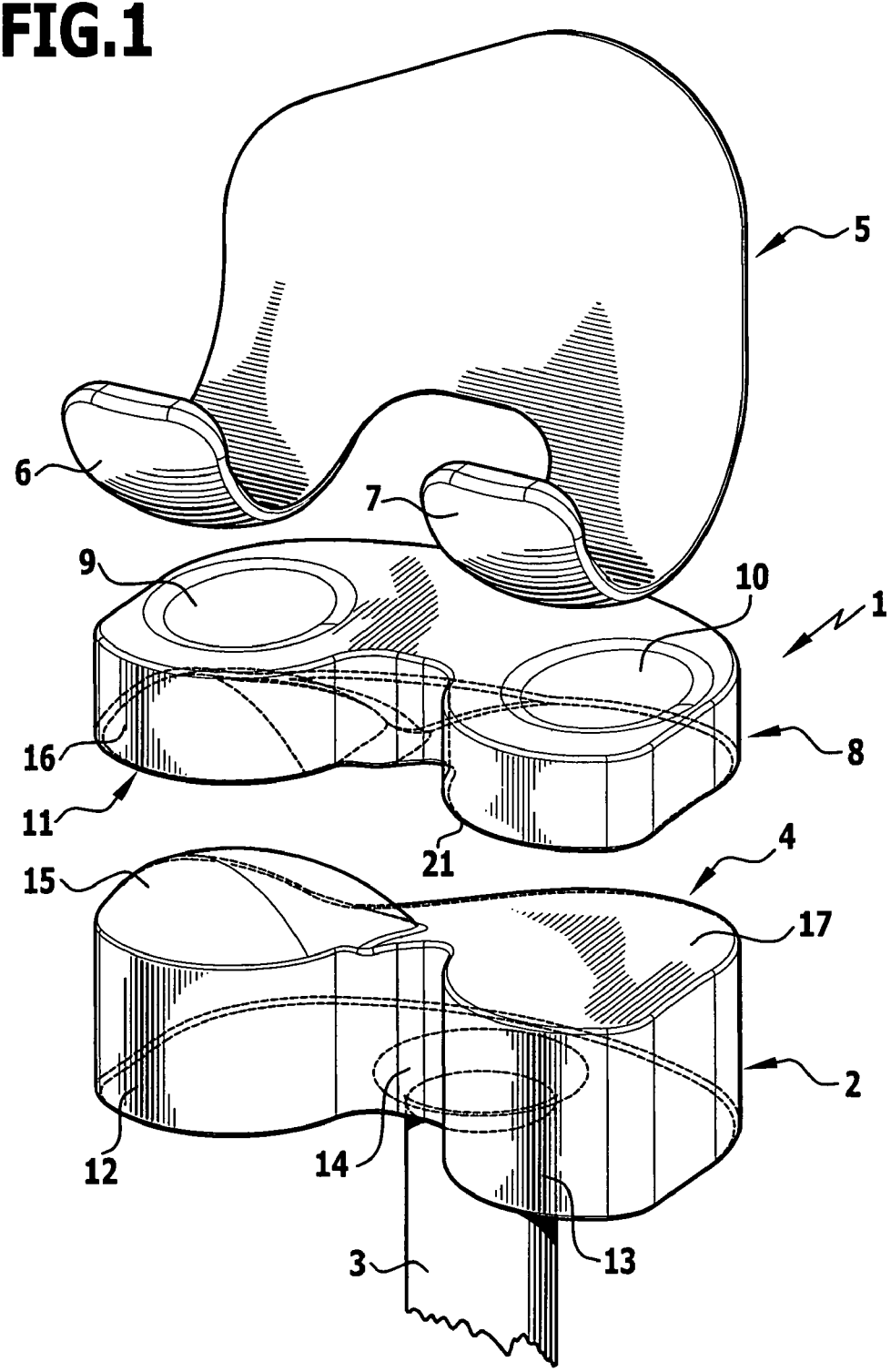
FIG. 1 shows a perspective schematic view of a tibia part and arranged at a spacing therefrom a meniscus part in a viewing direction onto the upper side of the tibia part.
Figure 2:
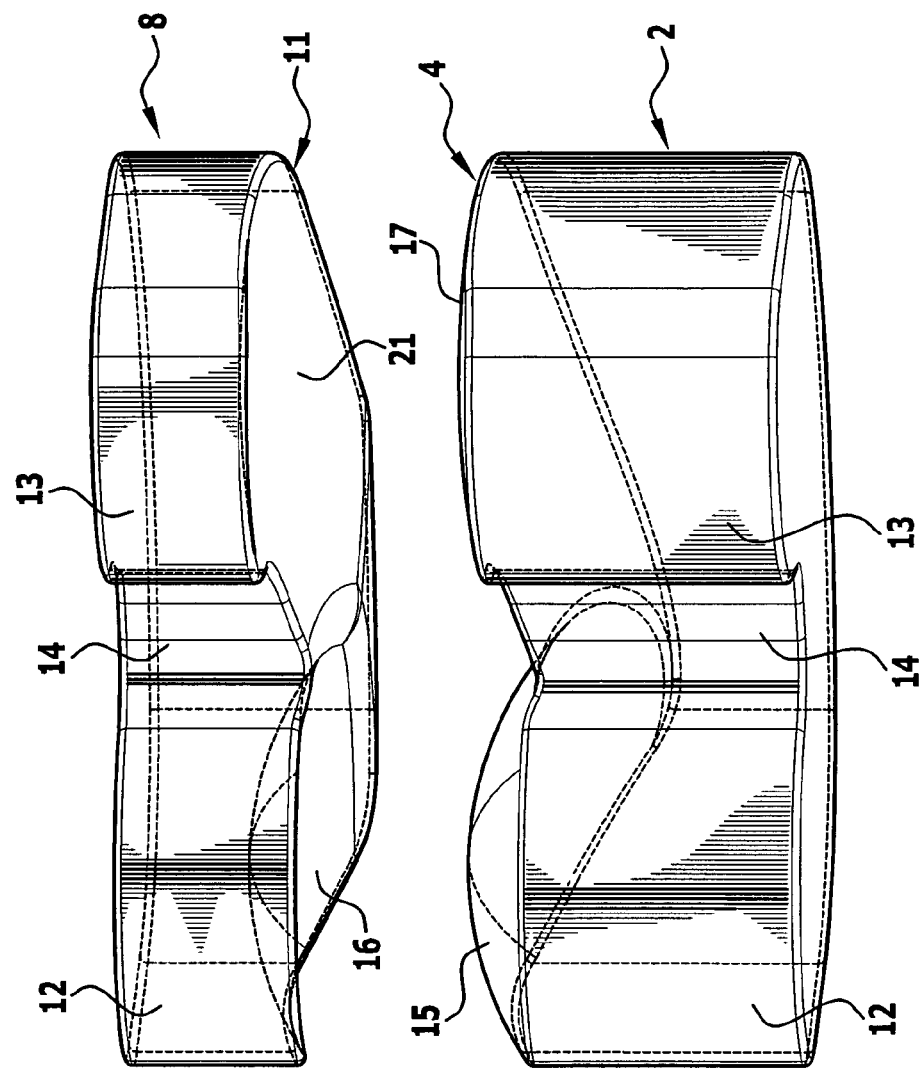
FIG. 2 shows a view similar to FIG. 1 with a viewing direction towards the underside of the meniscus part.
Figure 3:
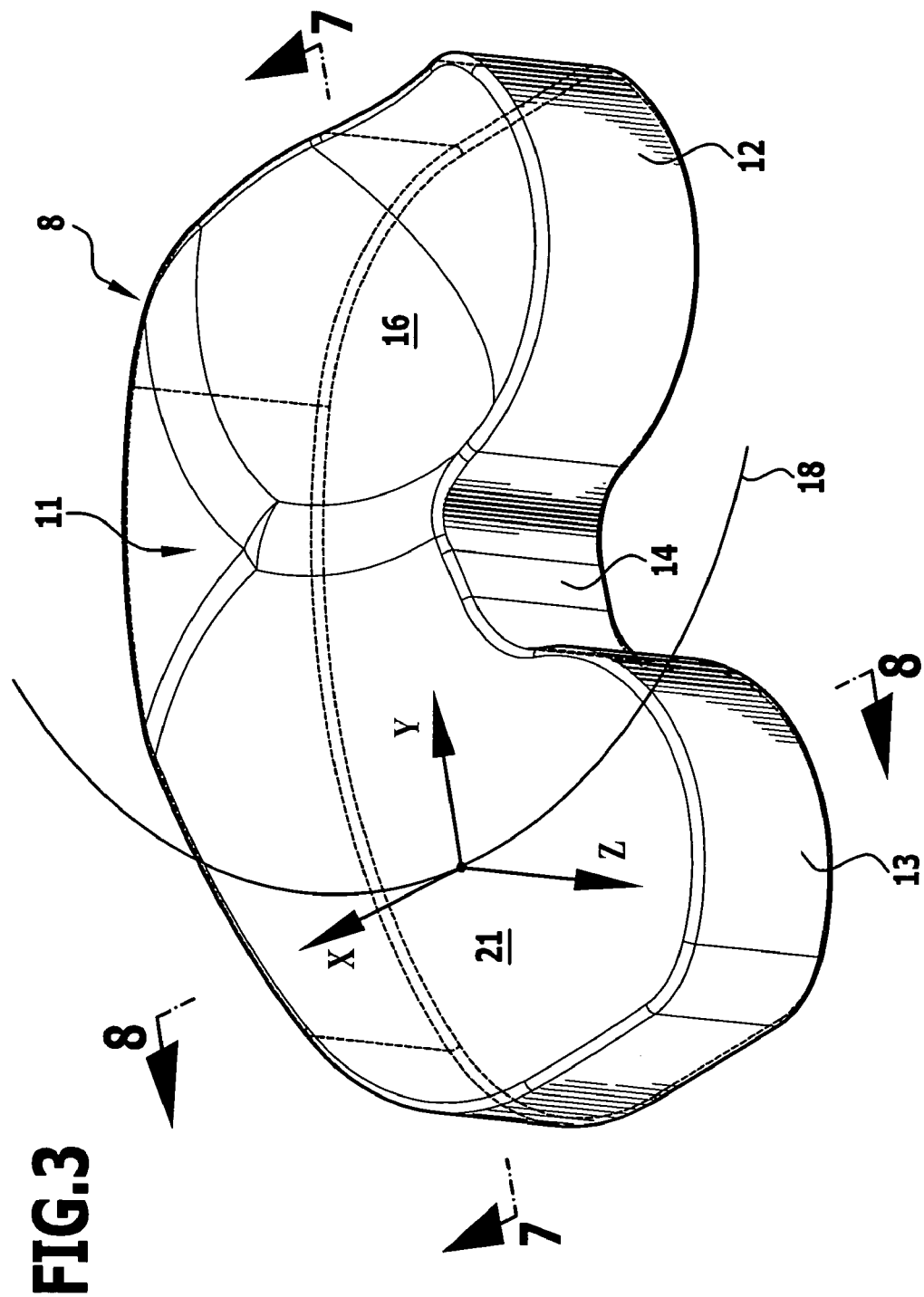
FIG. 3 shows a perspective view of the underside of the meniscus part.
Figure 4:
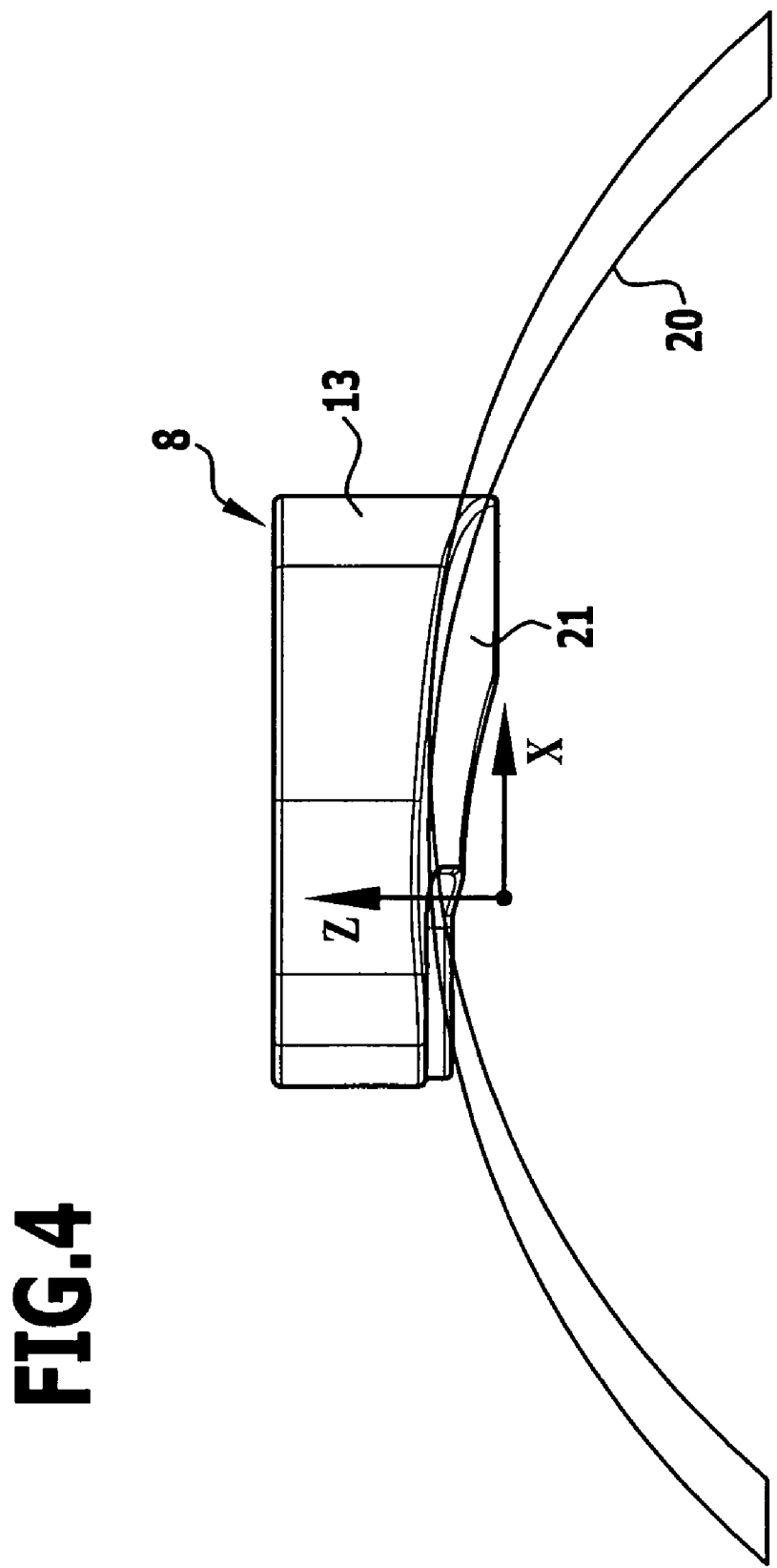
FIG. 4 shows a side view of the meniscus part with a cylinder surface to illustrate the curvature of the supporting area of the meniscus part in a dorsal-ventral direction.
Figure 5:
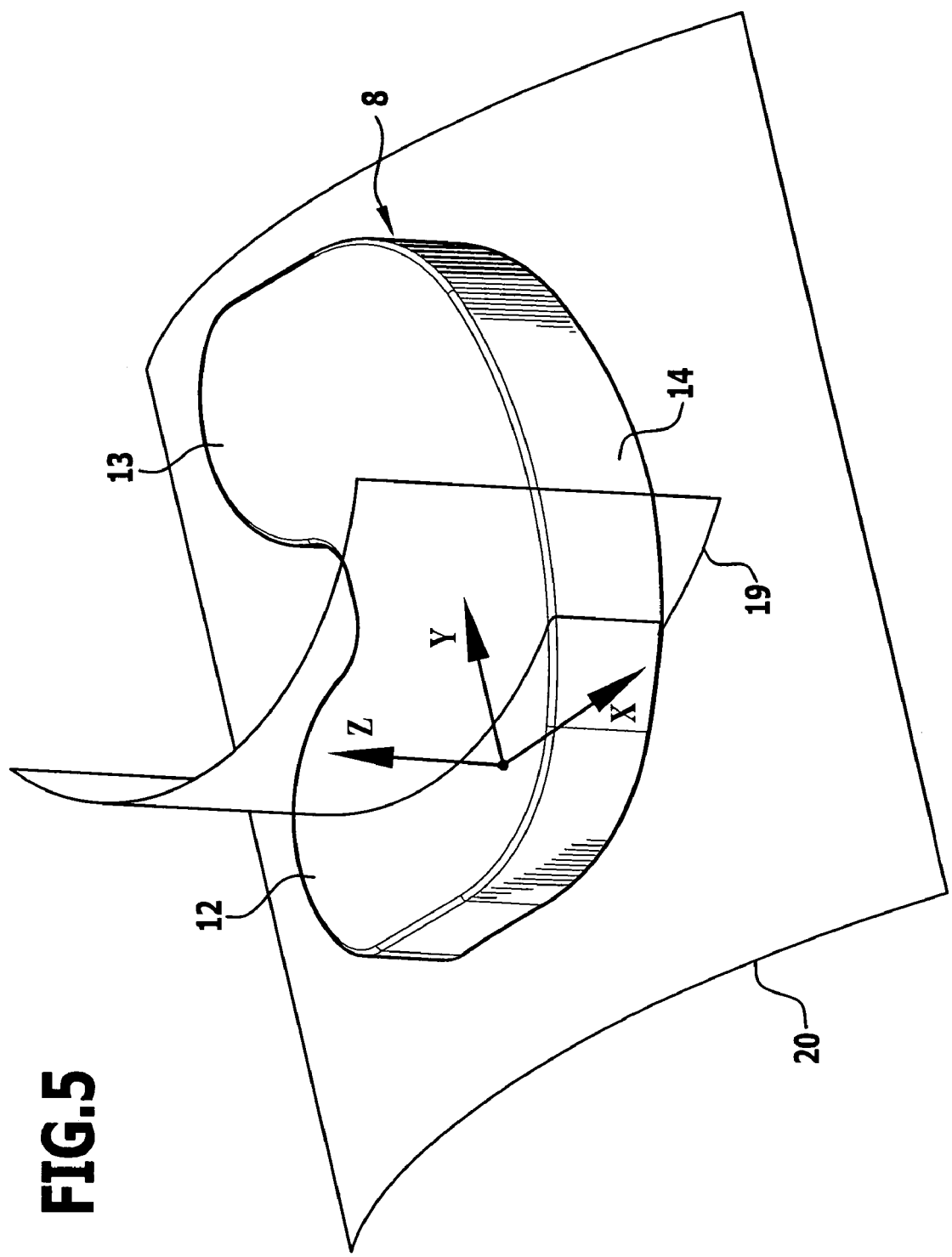
FIG. 5 shows a perspective plan view of the meniscus part with the cylinder surface of FIG. 4 and, in addition, a cylinder surface of a perpendicular cylinder which is arranged coaxially with the axis of rotation of the meniscus part in relation to the tibia part.
Figure 6:
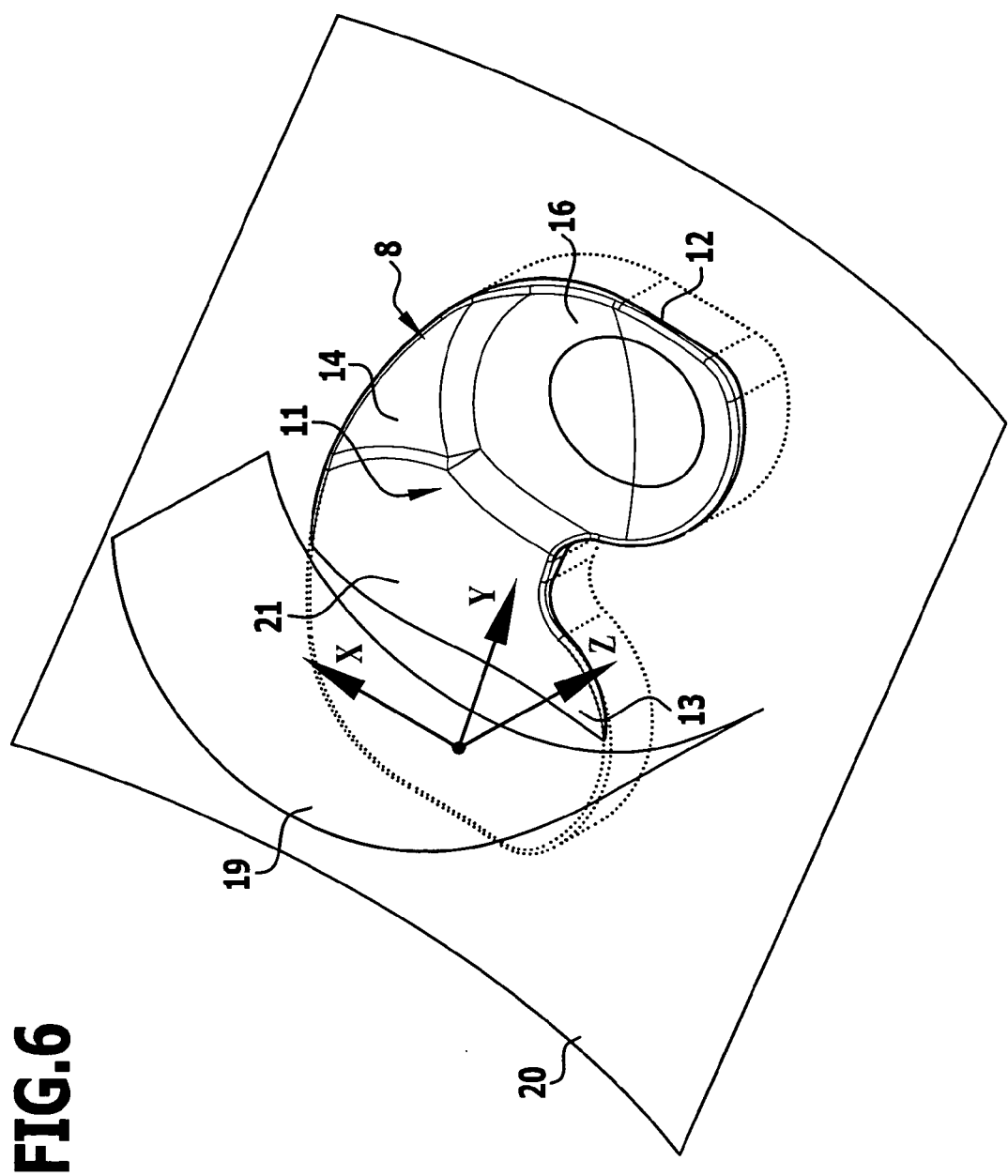
FIG. 6 shows a perspective view of the meniscus part of FIG. 5 from its underside with the two cylinder surfaces of FIG. 5 represented.
Figure 7:
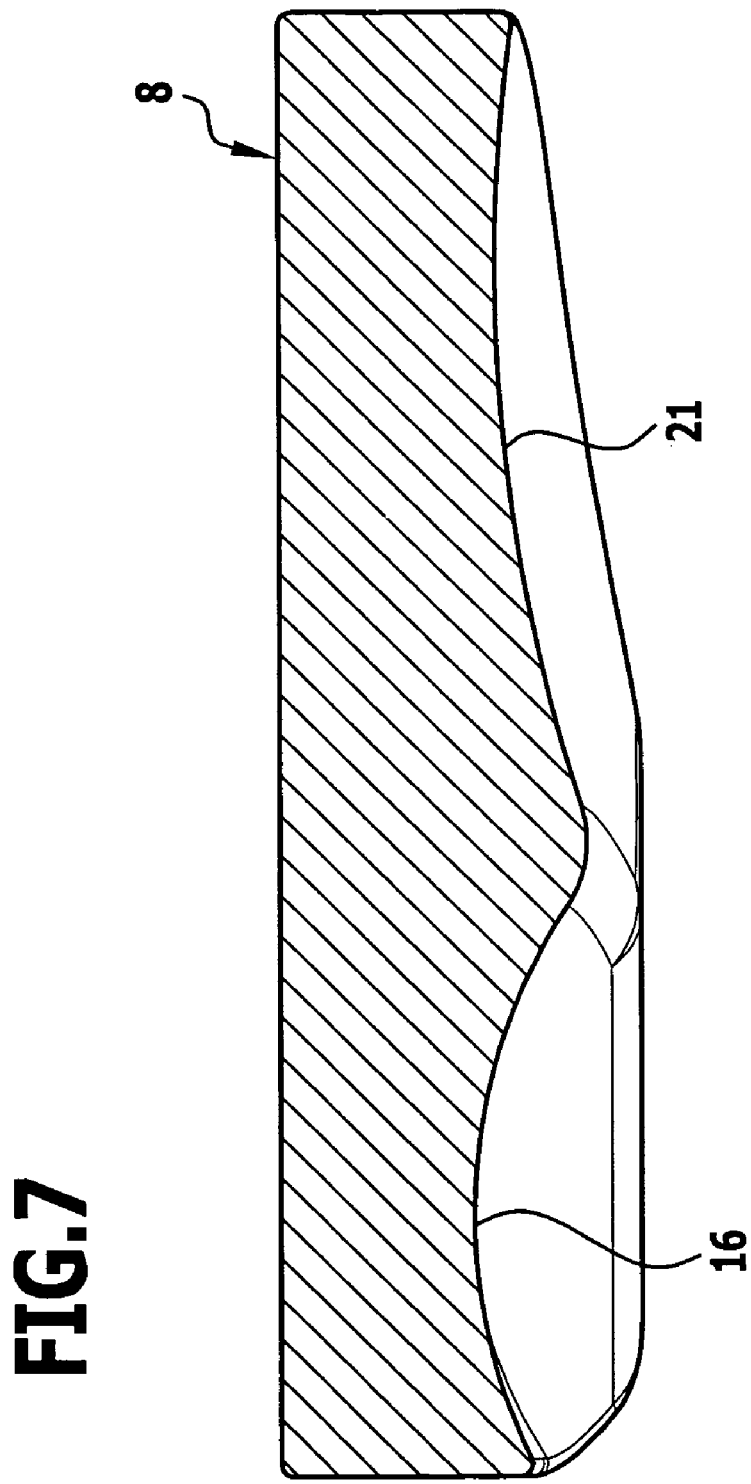
FIG. 7 shows a sectional view of the meniscus part of FIG. 3 taken along line 7-7 in FIG. 3.

The knee endoprosthesis 1 shown in FIG. 1 comprises a tibia part 2 with a shank 3 for securing the tibia part 2 to a tibia and with an upper side serving as bearing surface 4, also a femur part 5 for anchorage at the distal end of a femur with two curved condylar surfaces 6, 7 lying next to each other, and arranged between the tibia part 2 and the femur part 5 a meniscus part 8, with two bearing shells 9, 10 arranged next to each other on its upper side, in which the condylar surfaces 6, 7 engage, and with a meniscus-bearing surface 11 on the underside of the meniscus part 8.

The condylar surfaces 6, 7 can be displaced in the bearing shells 9, 10 such that, firstly, a pivotal movement of the femur relative to the tibia is possible, and, secondly, a lateral displacement of the condylar surfaces 6, 7 in the longitudinal direction of the bearing shells 9, 10 is also possible to a certain extent. This enables a combined rolling-and-sliding movement between meniscus part 8, on the one hand, and femur part 5, on the other hand. Since the configuration of the bearing shells 9, 10 and the condylar surfaces 6, 7 is not of paramount importance for the present invention, the bearing shells 9, 10 and the femur part 5 with the condylar surfaces 6, 7 are only shown in FIG. 1. The representation is limited to the meniscus part 8 and the tibia part 2 (without shank) in the subsequent Figures, where the bearing shells 9, 10 are not shown on the upper side of the meniscus part 8, but rather the upper side of the meniscus part 8 is depicted flat. In reality, however, a configuration in accordance with the representation in FIG. 1 with bearing shells 9, 10 on the upper side is to be assumed.

Both the tibia part 2 and the meniscus part 8 are of essentially U-shaped construction with two side parts 12, 13 lying next to each other and a web-shaped intermediate part 14 joining these. The tibia-bearing surface 4 has in the medial side part 12 on its upper side a spherical projection 15. The center point of the spherical projection 15 is, in relation to the center of the tibia part 2, which lies between the two side parts 12, 13, offset in a medial direction and is located approximately at the center of the medial side part 12. The radius of the spherical projection 15 lies in the range of between 20 mm and 30 mm, preferably in the range of between 22 mm and 26 mm.

In the medial side part 12 of the meniscus part 8 there is located a recess 16 which is complementary to the projection 15 and in which the projection 15 engages when the meniscus part 8 lies directly on the tibia part 2. A ball bearing-like mounting between the tibia part 2, on the one hand, and the meniscus part 8, on the other hand, is thereby formed. Firstly, owing to this mounting, the meniscus part 8 can be rotated about an axis of rotation which extends substantially parallel to the tibial longitudinal axis and is, therefore, arranged substantially perpendicular to the upper side of the meniscus part 8. It is, however, also possible, owing to this ball bearing-like mounting, to pivot the meniscus part relative to the tibia part, for example, about a pivot axis extending in a medial-lateral direction.

In the area of the lateral side part 13, the upper side of the tibia part 2 is constructed as a supporting area 17. In this supporting area, the tibia-bearing surface 4 has a curved contour, more specifically, this supporting area 17 is curved both in a ventral-dorsal direction and in a medial-lateral direction. In both cases, the curvature in the embodiment shown in the drawings is so selected that the centers of curvature lie below the supporting area 17. The radius of curvature is relatively large in both curvatures. In the embodiment shown, the radius of curvature in a ventral-dorsal direction is larger than the radius of curvature of the spherical projection 15 and the spherical recess 16 by the factor 2.5. In a lateral-dorsal direction, the radius of curvature of the supporting area 17 is greater than the radius of curvature of the projection 15 and the recess 16 by approximately the factor 2.5 to 3.

Different choices are possible for the exact contour of the supporting area 17. For example, the curvatures in a ventral-dorsal direction can be identical to the curvatures in a medial-lateral direction, with the result that essentially a spherical supporting area 17 is obtained. It is, however, also possible for the supporting area 17 to have the shape of a torus, but a torus whose longitudinal axis is additionally curved out of the plane in circumferential direction, thereby corresponding to the curvature in a ventral-dorsal direction.

A special shape is chosen for the supporting area 17 in the embodiment shown in the drawings. This supporting area 17 is built up by a plurality of lines of intersection 18, which result from the penetration of two cylinders, namely a perpendicular cylinder 19 and a horizontal cylinder 20.

The perpendicular cylinder 19 has a longitudinal center line which passes through the highest point of the projection 15 and extends substantially parallel to the tibial longitudinal axis. This axis forms the axis of rotation of the meniscus part 8 in relation to the tibia part 2 when these parts are rotated relative to each other.

The horizontal cylinder 20 describes the curvature in a dorsal-ventral direction, the longitudinal center line of the horizontal cylinder 20 extends in a lateral-medial direction, and the radius of the horizontal cylinder 20 corresponds to the radius of curvature of the curvature of the supporting area 17 in a dorsal-ventral direction. There result between the horizontal cylinder 20 and the perpendicular cylinder 19 with different radius a plurality of lines of intersection 18, which then jointly build up the supporting area 17.

The meniscus-bearing surface 11 is complementary in construction to the tibia-bearing surface 4, so that when the meniscus part 8 bears on the tibia part 2, there is contact over substantially the whole surface, firstly, in the area of the projection 15 and the recess 16 and, secondly, in the area of the supporting area 17. In this supporting area 17, the meniscus part 8 bears thereon with a supporting area 21 which is complementary to the supporting area 17.

Owing to the mounting described, it is possible, when horizontal forces are exerted on the meniscus part 8, for the meniscus part 8 to move relative to the tibia part 2, more specifically, firstly, in the form of rotational movement about the axis of rotation, which coincides substantially with the center axis of the perpendicular cylinder 19, and, secondly, by pivotal movement of the meniscus part 8 about a horizontal pivot axis extending substantially perpendicularly on the wall of the perpendicular cylinder 19. In a central position, this pivot axis thus extends substantially in a lateral-medial direction. Upon rotation of the meniscus part 8 relative to the tibia part 2, this pivot axis is also rotated in accordance with the angle of rotation, and, in the case of rotation, too, this results in the meniscus part bearing on the tibia part over substantially the whole surface. At the same time, the meniscus part is pivoted about this pivot axis during this rotation, so that the respectively outward lying edge is lowered, and the joint is thereby given clearance for a larger bending angle.

The rotational movement about the axis of rotation thus always takes place about an axis of rotation which is arranged off-center and is offset in a medial direction. The pivotal movement takes place additionally in a positively guided manner about a pivot axis which extends substantially horizontally and changes its angle in relation to the medial-lateral direction with the angle of rotation of the meniscus part.

The forces which result in a displacement of the meniscus part relative to the tibia part are essentially transmitted by the femur part onto the meniscus part when the joint is bent. In particular, the condylar surfaces 6, 7 thus transmit via the bearing shells 9, 10 such forces as result in a rotational movement and a pivotal movement of the meniscus part relative to the tibia part.

The tibia part 2 and the femur part 5 normally consist, in a manner known per se, of a body-compatible metal, for example, of titanium or of a titanium alloy, whereas the meniscus part preferably consists of a sterilizable and body-compatible plastic material, for example, of low density polyethylene. Owing to the described shape given to the bearing surfaces, a contact over the whole surface in the area between the tibia part and the meniscus part is achieved, and this results in the avoidance of force peaks and in the reduction of wear on the bearing surfaces bearing on one another.

In the embodiment shown in the drawings, the projection 15 and the recess 16 are offset in a medial direction, the supporting area, in contrast, in a lateral direction, in relation to the center of the bearing surface. In principle, it is also possible for a reverse arrangement to be chosen. The projection 15 and the recess 16 are then offset in a lateral direction, and the supporting region 17, in contrast, in a medial direction. As a result, the axis of rotation of the meniscus part 8 is, of course, also displaced accordingly. The arrangement of the axis of rotation in the medial part of the bearing surface is more often the case, it may, however, prove necessary—particularly on account of a change in the ligamentous structure—for the axis of rotation to be offset not in a medial direction but in a lateral direction in relation to the center of the bearing surface.

The invention claimed is:

1. Knee endoprosthesis comprising:
   a tibia part having on an upper side a tibia-bearing surface;
   a femur part having two condylar surfaces; and
   a meniscus part arranged between said femur part and said tibia part;
   said meniscus part having on an upper side two bearing shells for receiving and mounting the condylar surfaces of said femur part and having on an underside a meniscus-bearing surface which rests in a displaceable manner on the tibia-bearing surface;
   said meniscus-bearing surface comprising one of a spherical projection or a spherical recess offset in one of a medial or a lateral direction in relation to a center of the meniscus-bearing surface; and
   said tibia-bearing surface comprising the other of the spherical projection or the spherical recess offset in the corresponding medial or lateral direction of the tibia-bearing surface, such that the spherical projection on one of said two bearing surfaces engages the spherical recess of the other bearing surface and thereby forms a ball bearing-like mounting of said meniscus part on said tibia part which is offset in the corresponding medial or lateral direction of the bearing surfaces; and
   wherein:
      in the other of the lateral or medial direction of said two bearing surfaces, the two bearing surfaces each form corresponding supporting areas which bear on each other,
      the supporting areas are correspondingly curved in a dorsal-ventral direction and have a radius of curvature which is greater than a radius of curvature of said spherical projection and said spherical recess by at least the factor 2.5,
      the supporting areas of the two bearing surfaces are also curved in a lateral-medial direction, and
      the supporting areas extend along one or more lines, which result as lines of intersection of two cylinder surfaces, namely a perpendicular cylinder surface having a center axis which passes through a center point of the spherical projection and the spherical recess and extends substantially parallel to a tibial longitudinal axis, and a horizontal cylinder surface having a center axis which passes through a center point defined by the curvature extending in the dorsal-ventral direction and extends substantially in a medial-lateral direction.

2. Knee endoprosthesis in accordance with claim 1, wherein the supporting areas of the two bearing surfaces are parts of a spherical surface whose radius is greater than the radius of the spherical projection and the spherical recess by at least the factor 2.5 to 3, the center points of the spherical projection and the spherical recess being offset in the medial direction and center points of the spherical surfaces being offset in the lateral direction in relation to the center of the bearing surfaces.

3. Knee endoprosthesis in accordance with claim 2, wherein the projection and the recess and the supporting areas extend substantially as far as a common horizontal plane of the meniscus part.

4. Knee endoprosthesis in accordance with claim 1, wherein the projection and the recess and the supporting areas extend substantially as far as a common horizontal plane of the meniscus part.

* * * * *